(12) United States Patent
Jackson

(10) Patent No.: US 6,822,405 B2
(45) Date of Patent: Nov. 23, 2004

(54) DECELERATION OF HADRON BEAMS IN SYNCHROTRONS DESIGNED FOR ACCELERATION

(76) Inventor: Gerald P. Jackson, 6380 New Albany Rd., Lisle, IL (US) 60532-3235

( * ) Notice: Subject to any disclaimer, the term of this patent is extended or adjusted under 35 U.S.C. 154(b) by 0 days.

(21) Appl. No.: 10/408,866

(22) Filed: Apr. 7, 2003

(65) Prior Publication Data

US 2003/0210002 A1 Nov. 13, 2003

Related U.S. Application Data

(60) Provisional application No. 60/370,605, filed on Apr. 5, 2002, provisional application No. 60/388,428, filed on May 29, 2002, provisional application No. 60/382,042, filed on May 20, 2002, now abandoned, and provisional application No. 60/316,711, filed on Aug. 30, 2001.

(30) Foreign Application Priority Data

Aug. 29, 2002 (WO) .............................. PCT/US02/27796

(51) Int. Cl.⁷ ...................... H05H 15/00; H05H 11/00; H05H 13/00
(52) U.S. Cl. ........................................ 315/503; 315/601
(58) Field of Search ................................. 315/504, 501, 315/503, 500; 250/489, 492.1, 493.1

(56) References Cited

U.S. PATENT DOCUMENTS

| | | | | | |
|---|---|---|---|---|---|
| 4,491,948 A | * | 1/1985 | Deacon et al. | ................. | 372/2 |
| 5,001,437 A | * | 3/1991 | Miyata et al. | .............. | 315/501 |
| 5,073,913 A | * | 12/1991 | Martin | ........................ | 378/34 |
| 5,138,271 A | * | 8/1992 | Ikegami | ...................... | 315/501 |
| 5,363,008 A | * | 11/1994 | Hiramoto et al. | ............. | 313/62 |
| 5,557,178 A | * | 9/1996 | Talman | ...................... | 315/501 |
| 6,265,837 B1 | * | 7/2001 | Akiyama et al. | .......... | 315/503 |
| 6,606,370 B1 | * | 8/2003 | Kasprowicz | ................ | 376/113 |

* cited by examiner

*Primary Examiner*—Don Wong
*Assistant Examiner*—Chuc Tran
(74) *Attorney, Agent, or Firm*—Peter K. Trzyna, Esq.

(57) ABSTRACT

A method for using a synchrotron, the method including the steps of: providing a synchrotron designed to accelerate a hadron beam to higher momenta; altering said synchrotron to enable deceleration of hadron beams to lower momenta; and using the synchrotron in said altering step in decelerating a hadron beam to lower momentum.

55 Claims, 9 Drawing Sheets

FIG. 4

DECELERATION OF HADRON BEAMS IN SYNCHROTRONS DESIGNED FOR ACCELERATION

CONTINUITY STATEMENT

This patent application is a Provisional, claiming priority from, and incorporated by reference, the following patent applications: "Antiproton Deceleration," Ser. No. 60/370,605, filed Apr. 5, 2002; "Real Time Detention of Delivery of Antiprotons for Therapeutic Use," Ser. No. 60/388,428, filed May 29, 2002; "Method for Investigating Use of Antiproton Beams in Clinical Radiotherapy," Ser. No. 60/382,042 filed May 20, 2002, now abandoned, and "Antiproton Production and Delivery for Imaging and Termination of Undesirable Cells" Ser. No. PCT/US02/27796, which in turn claims priority from a patent application Ser. No. 60/316,711 "Non-invasive Method of Cellular Termination Using Antiproton Reactions" filed Aug. 30, 2001, incorporated by reference.

BACKGROUND OF THE INVENTION

A. Field of the Invention

This invention relates to the field of hadron beams in synchrotrons designed for acceleration. More particularly, the present invention relates to a method for decelerating hadron beams using existing synchrotrons designed for acceleration. Even more specifically, the present invention relates to a method for decelerating antiprotons using existing synchrotrons designed for acceleration. More specifically, the present invention addresses the production of antiprotons; the collection and storage of antiprotons; the transport of antiprotons.

B. Background of the Invention

Hadron beams are typically accelerated using synchrotrons, cyclotrons, or linear accelerators. For example, at the Loma Linda proton therapy facility a synchrotron is employed once the protons are emitted by the ion source and pre-accelerated in a radio-frequency quadrupole (RFQ), while the Massachussetts General Hospital proton therapy facility employs a cyclotron. They accelerate protons up to a momentum of 0.73 GeV/c, which corresponds to the energy a proton needs to completely traverse a typical human chest cavity.

There are examples of synchrotrons specifically designed for deceleration of hadron beams. These include the LEAR and AD synchrotrons, both operated at the CERN particle physics laboratory in Geneva, Switzerland. These synchrotrons are used to perform scientic experiments with antiprotons.

A third category of synchrotrons, called storage rings, neither accelerate nor decelerate hadron beams to higher or lower momenta. Their purpose is to merely store the hadron beam at their original injection momentum.

Because the radius of curvature of a hadron beam traversing bending magnets is proportional to the beam momentum, and the cost of the synchrotron scales with its circumference, the synchrotron is designed such that the bending (dipole) magnets are at their maximum field strength at the maximum anticipated momentum. Therefore, storage rings always operate at the maximum strength of their magnets, while accelerating synchrotrons operated at maximum magnetic field strength only at the end of the acceleration process.

All mechanical and electrical systems have a finite dynamic range within which the components can operate. The same is true of synchrotrons. Due to limitations in magnetic material properties, power supply regulation, and radio frequency acceleration system frequency adjustability, synchrotrons traditionally are found to have a maximum momentum range of a factor of twenty. There is a great deal of literature devoted to this issue in the field of accelerator physics. This reality also explains why laboratories working in the fields of atomic, nuclear, and particle physics have accelerator chains composed of many synchrotrons. The Fermi National Accelerator Laboratory is an example, wherein there are three synchrotrons required to accelerate protons and antiprotons to a momentum of 950 GeV/c for particle physics research. The maximum momentum range of any of these synchrotrons is a factor of 17.

SUMMARY OF THE INVENTION

One aspect of the present invention has an object of providing a means to better decelerate hadron beams. The corresponding method for decelerating antiprotons opens many commercial applications. For example, antiproton irradiation has utility in a variety of fields, including the treatment of cancerous tissue and the generation of radio-isotopes within the body that are useful for imaging techniques and therapeutic treatment. In the present invention deceleration is implemented using a synchrotron.

A synchrotron is comprised of a ring of dipole magnets interspersed with quadrupole, sextupole, correction dipole magnets, and one or more radio frequency acceleration systems, the operation of which are all managed by a computer control system. The dipole magnets bend a hadron beam into a closed loop that repeatedly passes through the electromagnetic fields generated by the radio frequency acceleration system. Typically all dipole magnets are wired in series to ensure that every magnet has exactly the same electrical current, and therefore magnetic field strength, in it. One or more power supplies around the synchrotron are employed to provide this electrical current. The amount of electrical current generated by a power supply at any given momentum is determined by commands from the computer control system.

The quadrupole magnets, which focus and defocus the hadron beam in a fashion very similar to the concave and convex lens combination in a telephoto camera lens, make sure that the beam oscillates around the middle of the magnets rather than straying out of the synchrotron. The strength of the focusing and defocusing magnetic fields are adjusted to maintain a desired number of horizontal and vertical oscillations each turn (revolution) around the synchrotron. Typically all of the focusing quadrupoles are wired in series to ensure that every magnet has exactly the same electrical current and hence magnetic field strength. Similarly, all of the defocusing quadrupoles are also wired in series. Two or more power supplies around the synchrotron are employed to provide these two electrical currents. The amount of electrical current generated by a power supply at any given momentum is determined by commands from the computer control system.

The sextupole magnets are used to control the horizontal and vertical chromacities of the synchrotron. Every hadron beam has some non-zero momentum distribution width. Without sextupoles, every hadron with a different momentum would have a different number of horizontal and vertical oscillations per revolution, or horizontal and vertical tunes. The change in tune per unit change in momentum is called chromaticity. The natural chromaticity of a synchrotron without sextupoles is equal and opposite to the tune. But too keep the hadron beam in the synchrotron for the desired duration, it is necessary to impose sextupole magnetic fields that simultaneously reduce both the horizontal and vertical chromaticity to near zero. Typically there is one sextupole placed near every quadrupole, with sextupoles near focusing quadrupoles having one field and the sextupoles near defocusing quadrupoles having a nearly equal but opposite field. Typically, all of the focusing "focusing" sextupoles are wired in series to ensure that every magnet has exactly the same electrical current and hence magnetic field strength. Similarly, all of the "defocusing" sextupoles are also wired in series. Two or more power supplies around the synchrotron are employed to provide these two electrical currents. The amount of electrical current generated by a power supply at any given momentum is determined by commands from the computer control system.

The position and orientation of each magnet always has some tolerance of misalignment. In addition, the strength of every dipole magnet is not precisely equal. These accumulated errors cause the hadron beam to deviate away from the magnet centers. Dipole correction magnets are used to steer a hadron beam vertically and horizontally, correcting the overall beam trajectory. There is typically one horizontal dipole corrector magnet at each focusing quadrupole and one vertical dipole corrector magnet at each defocusing quadrupole. Because the distribution of errors is typically random and time variable, each dipole corrector magnet has a unique electrical current generated by a separate power supply. The amount of electrical current generated by a power supply at any given momentum is determined by commands from the computer control system.

In a linear accelerator, each hadron in the beam passes once through each radio frequency acceleration cavity supporting electromagnetic fields. Just as a surfer rides the edge of a wave to pick up speed, each charged hadron is accelerated or decelerated by riding either the leading or trailing edge of the electromagnetic waves. Each cavity and the multiple radio frequency amplifiers that power them are some of the most expensive elements of any particle accelerator. The innovation behind synchrotrons is that the hadron beam is looped around to reuse the same cavities multiple times, receiving momentum changes tens or hundreds of thousands of time per second. In this way, larger overall momentum changes are implemented at a fraction of the cost if implemented using a linear accelerator.

The importance of this invention, the modifying of a synchrotron designed for hadron beam acceleration in order to decelerate hadron beams, is the immense savings in time, manpower, and money over designing and building a dedicated synchrotron for deceleration. Whereas the construction of a new synchrotron can cost anywhere between $10 million and $1 billion, depending on the maximum momentum required, this modification of an existing synchrotron can cost as little as $10,000.

These and other features, objectives and advantages of the present improved invention will be readily understood upon consideration of the following detailed description of certain embodiments of the present improved invention and the accompanying drawings.

However, as a summary overview, the present invention provides a method for modifying an existing synchrotron designed for the acceleration of hadron beams to higher momenta, such that the synchrotron is enabled to decelerate hadron beams instead to lower momenta. These modifications can be made, for example, to certain synchrotron equipment and computer control system hardware and software to produce a counterintuitive use of a synchrotron designed for accelerating, i.e., decelerating.

Currently, antiprotons are generated and used in experimental studies of elementary particles physics. These experiments are typically performed at large particle accelerators, such as the Tevatron at the Fermi National Accelerator Laboratory (Fermilab). The Fermilab accelerator complex includes various linear accelerators and synchrotrons that are designed to generate antiprotons, to accelerate these antiprotons to very high energies and momenta (typically to 1 TeV), and to collide these antiprotons together with protons. The results of the collisions can be analyzed to provide information regarding the structure and physical laws of the universe.

While these experimental studies of particle physics use antiprotons with very high energies and momenta, other uses of antiprotons, such as the medical use, have relatively small energies and momenta. If the existing sources of antiprotons at such accelerators are to be used as sources of antiprotons for these other fields, the antiprotons have to be decelerated (i.e., energy and momentum of the antiprotons will have to be reduced). In addition, to provide antiprotons to locations that are off-site from the particle accelerators, the antiprotons have to be decelerated sufficiently to enable them to be stored in a portable synchrotron or cyclotron, or trapped in a container and transported to other locations. Because antiprotons are annihilated upon contacting matter, development has been performed to develop adequate containers (e.g., Penning traps) for transporting antiprotons. Further details regarding such methods are incorporated by reference, including: "Container for Transporting Antiprotons," U.S. Pat. No. 5,977,554 issued to Gerald A. Smith, et al. on Nov. 2, 1999; "Container for Transporting Antiprotons," U.S. Pat. No. 6,160,263 issued to Gerald A. Smith, et al. on Dec. 12, 2000.

Embodiments of the present invention decelerate the antiprotons by operating existing particle accelerators, which were designed to accelerate the antiprotons, under conditions that actually reduce the energy and momentum of the antiprotons. In sum, though, there is a method of decelerating antiprotons, the method comprising the steps of: providing antiprotons to a particle accelerator ring, the antiprotons having a first momentum distribution with a first average momentum; operating the particle accelerator ring so as to apply electromagnetic fields to the antiprotons as the antiprotons travel around the ring; and selectively applying the electromagnetic fields to the antiprotons as the antiprotons travel around the ring, such that the antiprotons have a second momentum distribution with a second average momentum less than the first average momentum. Another embodiment of this same idea can be phrased as a method for decelerating antiprotons includes providing antiprotons to a particle accelerator ring. The antiprotons have a first momentum distribution with a first average momentum. The method further includes operating the particle accelerator ring so as to apply electromagnetic fields to the antiprotons as the antiprotons travel around the ring. The method further includes selectively applying the electromagnetic fields to the antiprotons as the antiprotons travel around the ring such that the antiprotons have a second momentum distribution with a second average momentum less than the first average momentum.

BRIEF DESCRIPTION OF THE DRAWINGS

FIG. 4 is a modified instruction set in a dipole corrector power supply system (I:V101) control system interface card that enables control of the beam trajectory during decelerating of a beam.

DESCRIPTION OF THE PREFERRED EMBODIMENT

Figure 1:
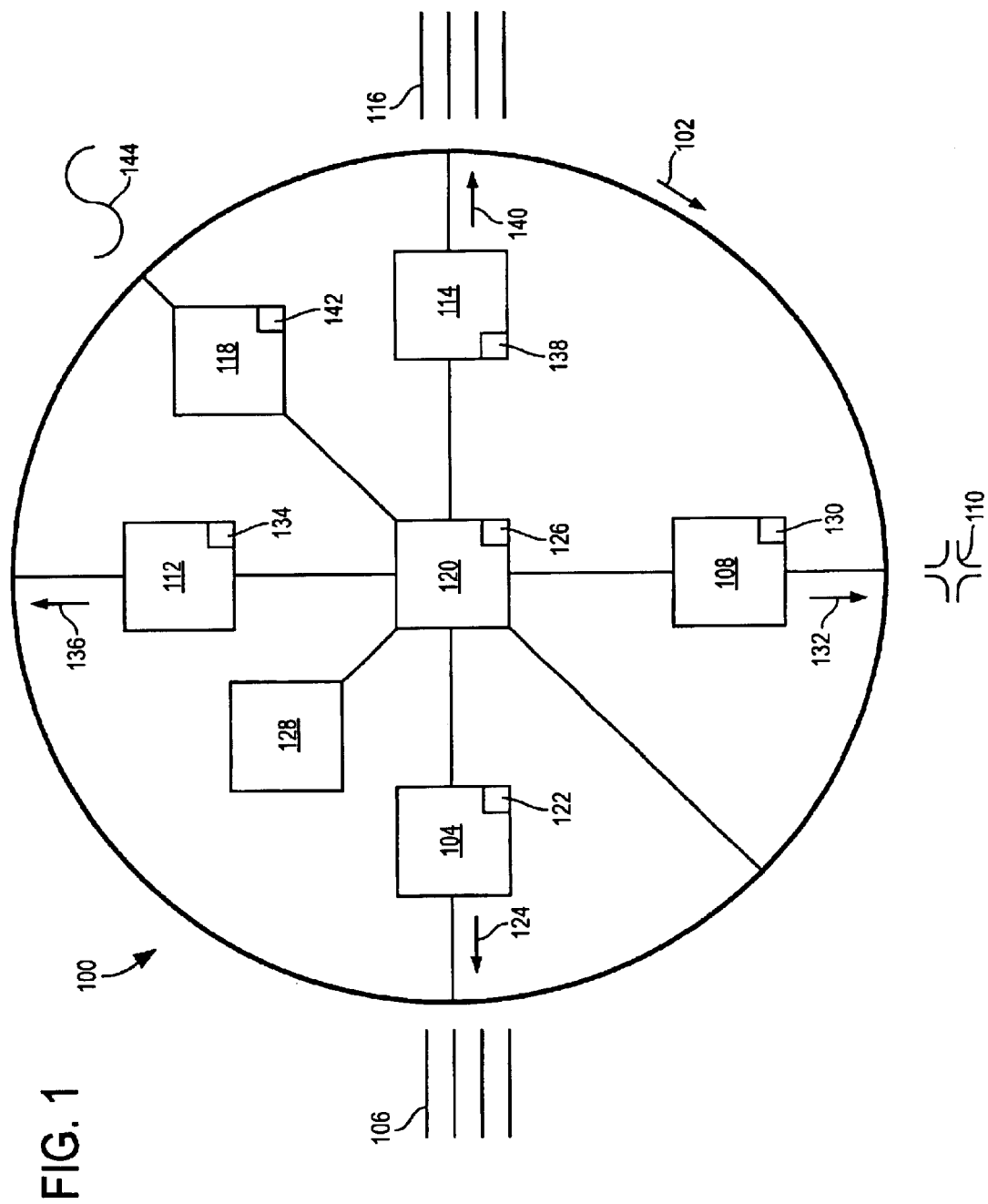
FIG. 1 is a schematic representation of a synchrotron in accordance with the present invention.

FIG. 1 shows a synchrotron 100 designed to accelerate a hadron beam 102 to higher momenta. A method of altering the synchrotron to enable the unanticipated operation of decelerating said hadron beam to lower momenta is the subject of this invention. This method of altering can include modifying a dipole power supply system 104 in order to reduce the strength of a dipole magnetic field 106 during the decelerating of the hadron beam; modifying a quadrupole power supply system 108 in order to reduce the strength of focusing and defocusing magnetic fields 110 during the decelerating of the hadron beam; modifying a sextupole power supply system 112 in order to maintain chromaticity control during the decelerating of the hadron beam; modifying a dipole corrector power supply system 114 in order to reduce the strength of a trajectory correction magnetic field 116 during the decelerating of the hadron beam; modifying a radio frequency acceleration system 118 to impose phase stable momentum reduction during the decelerating of the hadron beam; and modifying a computer control system 120 of the synchrotron to enable the decelerating of the hadron beam.

Figure 2:
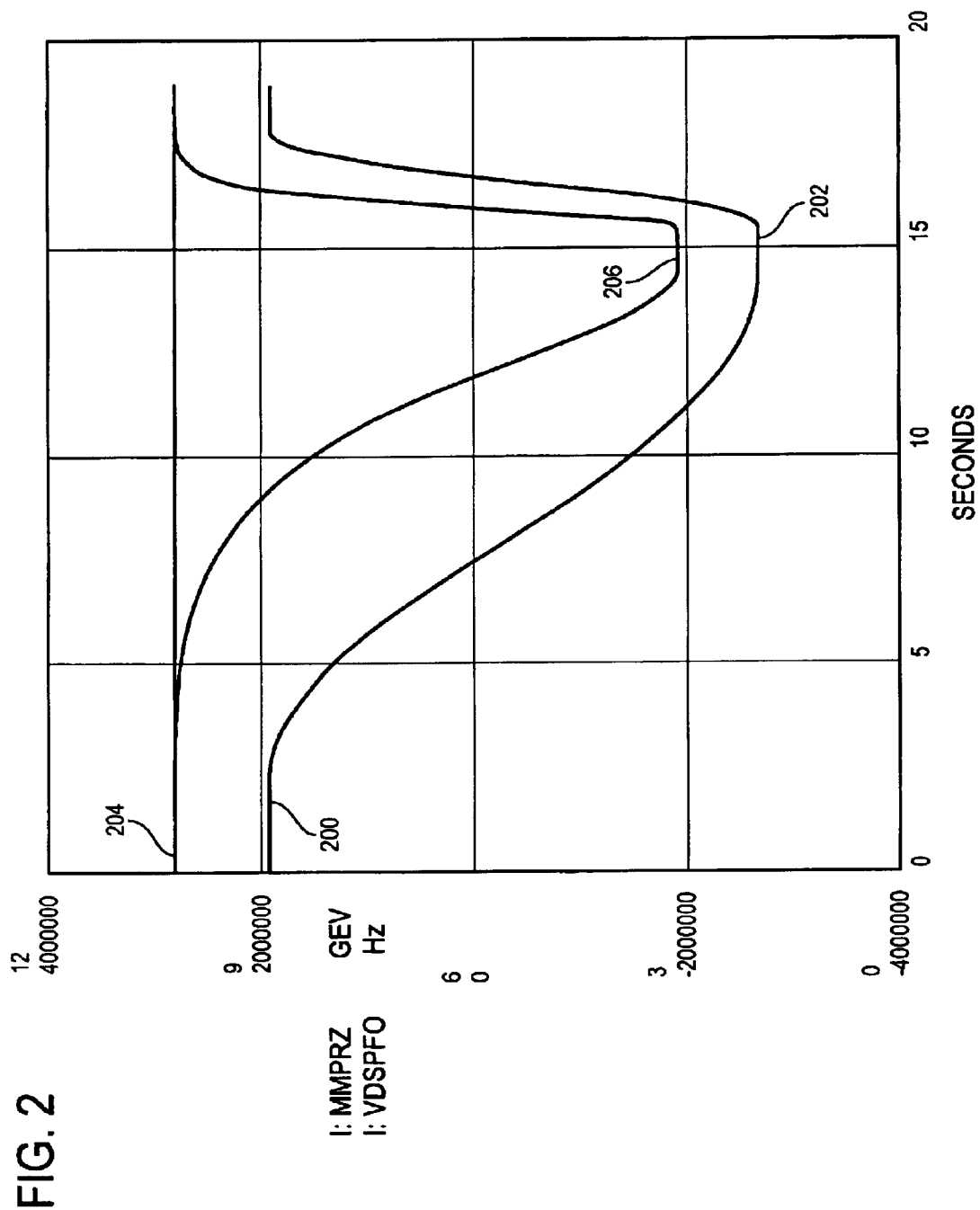
FIG. 2 is beam momentum (I:MMPRQ) and radio frequency acceleration system frequency (I:VDSPF0) vs. time.

FIG. 2 shows the result of a proton injected into the synchrotron at the nominal injection momentum 200. After the method of altering the synchrotron 100 is completed, the proton beam is decelerated to a lower momentum 202.

Figure 6:
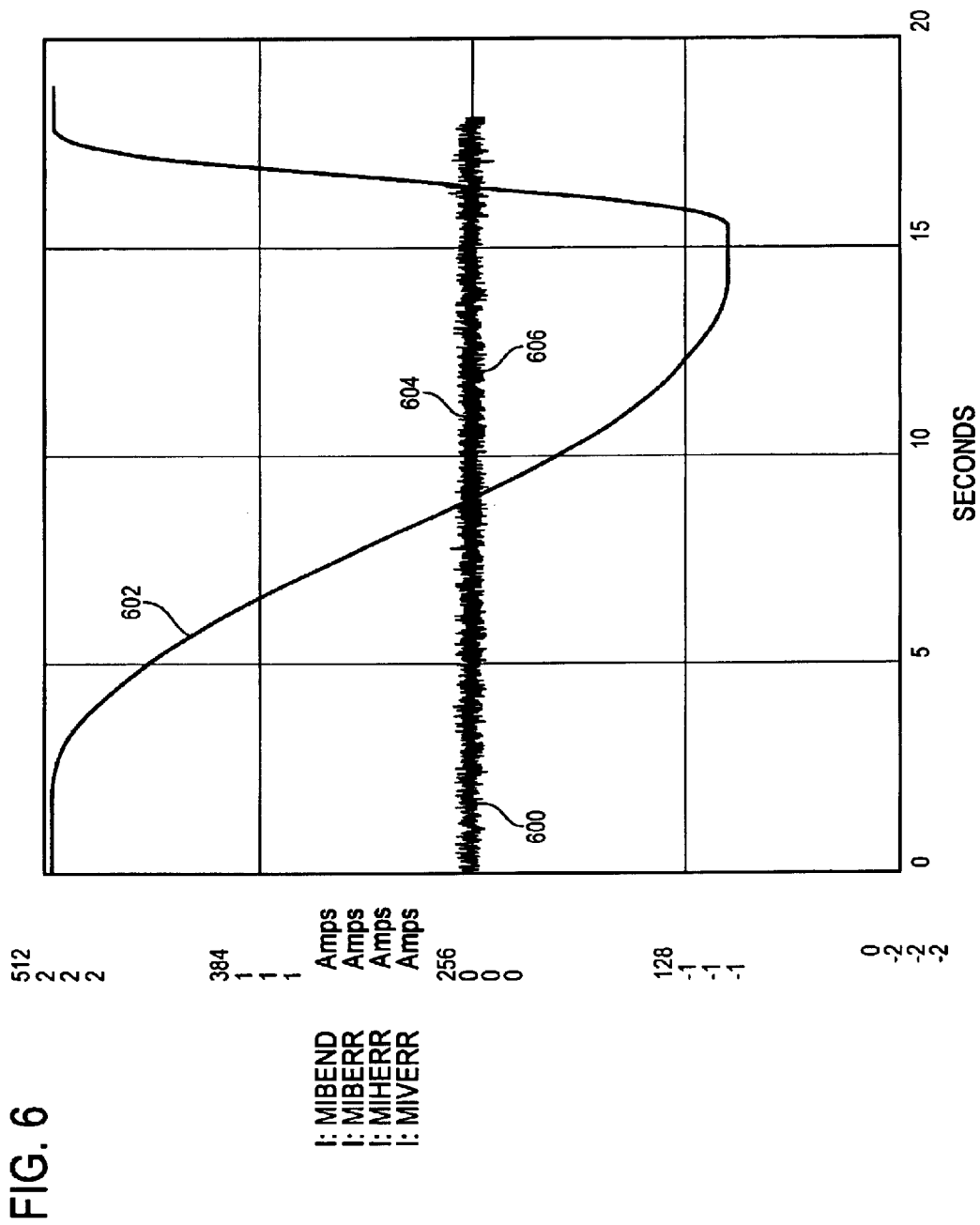
FIG. 6 is dipole power supply system electrical current (I:MIBEND), dipole power supply system error signal (I:MIBERR), focusing quadrupole power supply system error signal (I:MIHERR), and defocusing quadrupole power supply system error signal (I:MIVERR) vs. time.

The step of modifying a dipole power supply system 104 can include adding, removing, or altering a dipole power supply component 122 to ensure that the electric current 124 from the dipole power supply system follows commands from a computer control system 26. It can also include the adding, removing, or altering a computer control system component 126. It can also include the altering of a value of a variable in a computer control system database 128. In one embodiment of this invention, the step of modifying is performed in order to ensure that the dipole power supply error signal 600, the difference between the input command and output current 602 named I:MIBERR in FIG. 6, remains small over many hours.

Figure 9:
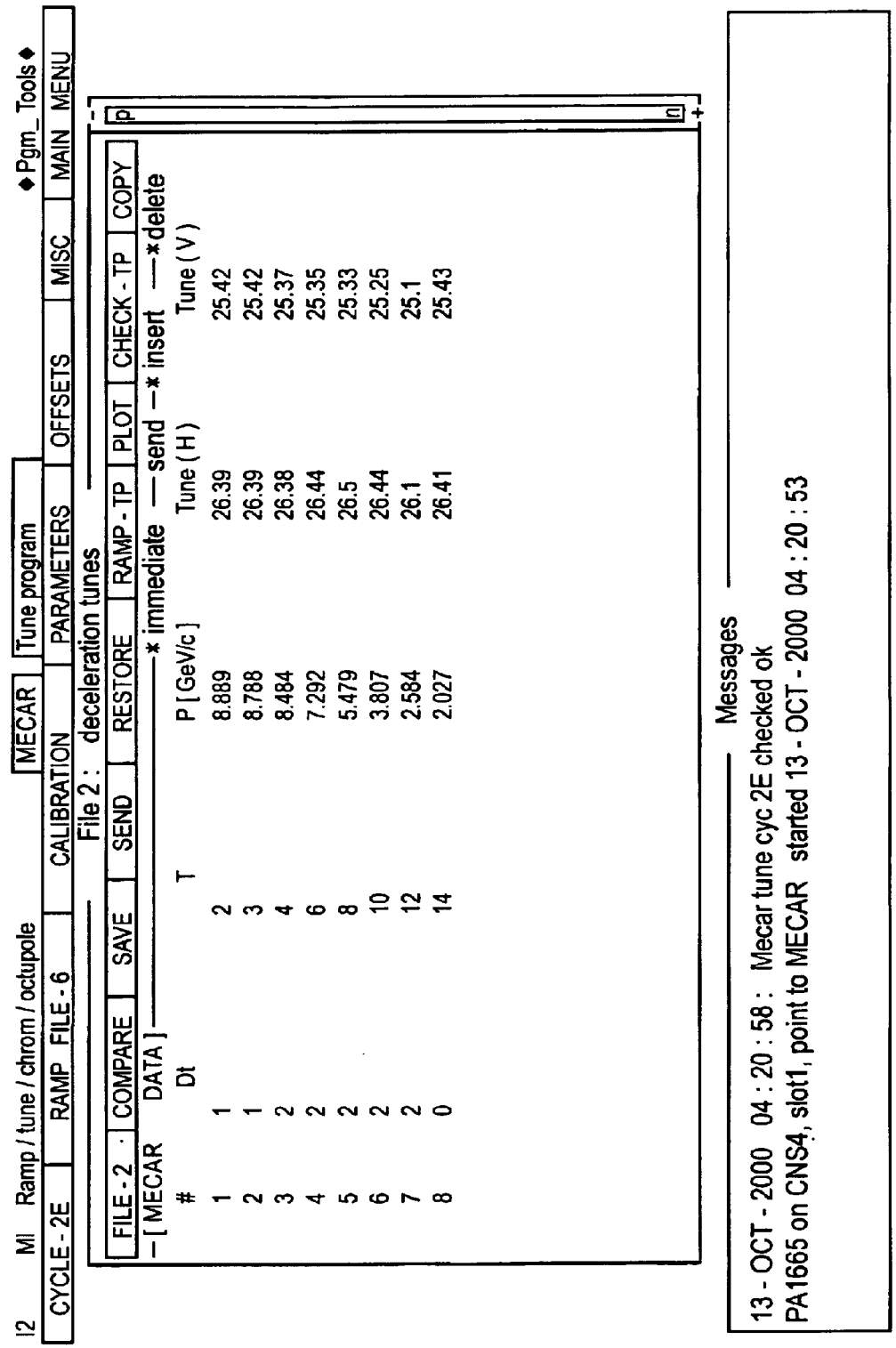
FIG. 9 is a modified instruction set in two quadrupole power supply control system interface cards that enables control of focusing and defocusing magnetic fields during decelerating of a beam.

The step of modifying a quadrupole power supply system 108 can include adding, removing, or altering a quadrupole power supply component 130 to ensure that the electric current 132 from the quadrupole power supply system follows commands from a computer control system 126. It can also include the adding, removing, or altering a computer control system component 126. It can also include the altering of a value of a variable in a computer control system database 128. In one embodiment of this invention, the step of modifying is performed in order to ensure that the quadrupole power supply error signals (604 for the focusing quadrupole power supply I:MIHERR and 606 for the defocusing quadrupole power supply I:MIVERR), the difference between the input command and output current, remain small over many hours. FIG. 9 demonstrates one embodiment of this invention in which computer control system variables are modified in order to control two quadrupole power supplies during the decelerating of a proton beam.

The step of modifying a sextupole power supply system 112 can include adding, removing, or altering a sextupole power supply component 134 to ensure that the electric current 136 from the sextupole power supply system follows commands from a computer control system 126. It can also include the adding, removing, or altering a computer control system component 126. It can also include the altering of a value of a variable in a computer control system database 128.

Figure 4:
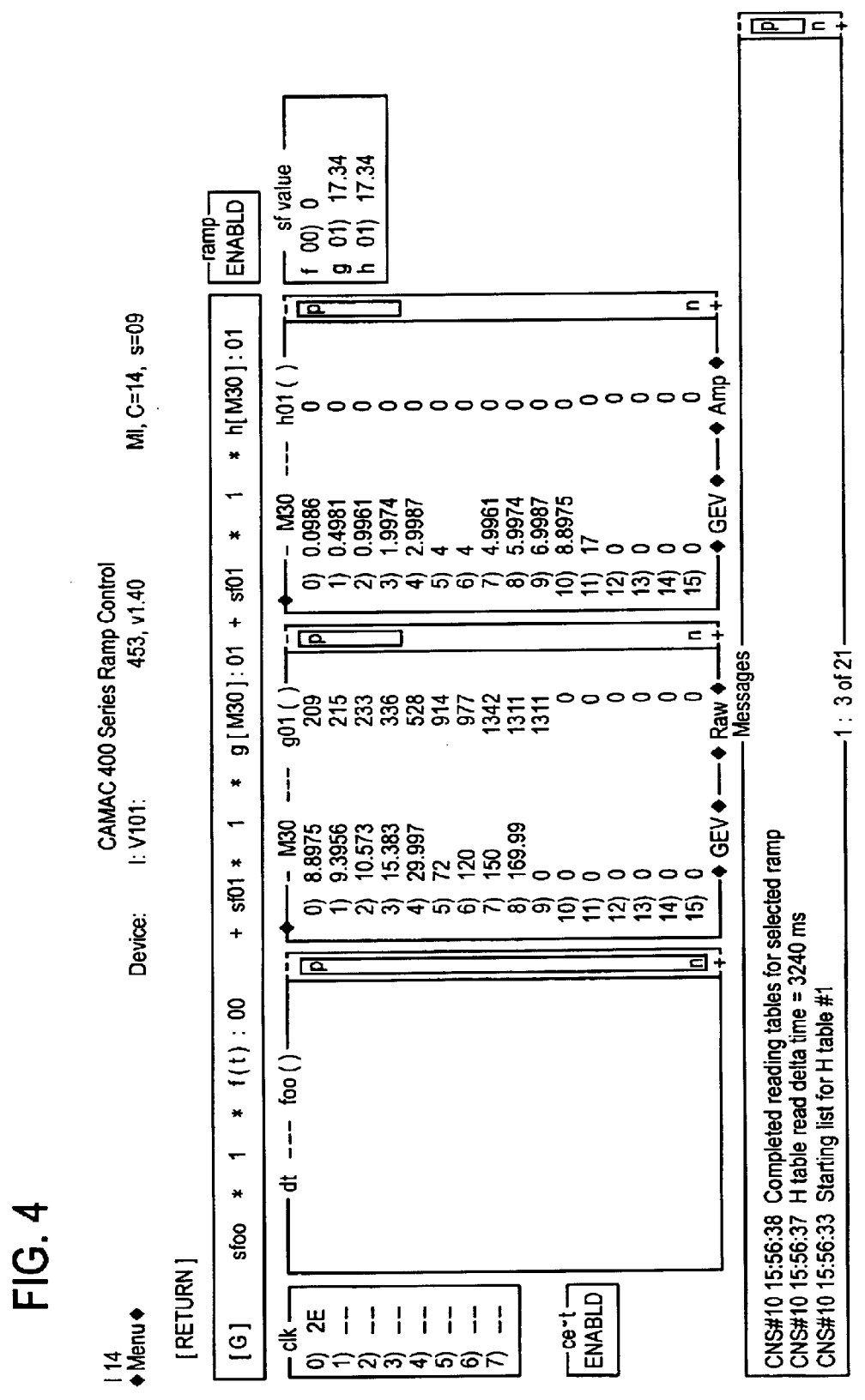

The step of modifying a dipole corrector power supply system 114 can include adding, removing, or altering a dipole corrector power supply component 138 to ensure that the electric current 140 from the quadrupole power supply system follows commands from a computer control system 126. It can also include the adding, removing, or altering a computer control system component 126. It can also include the altering of a value of a variable in a computer control system database 128. In one embodiment of this invention, the step of modifying is performed in order to ensure that the dipole corrector power supply system can move the hadron beam around any obstruction or misalignment of the synchrotron at any time during the decelerating of the hadron beam. FIG. 4 demonstrates how computer control system variables can be modified in order to control the dipole corrector power supply electric current 500 shown in FIG. 5 used to create a trajectory correction magnetic field 116.

Figure 3:
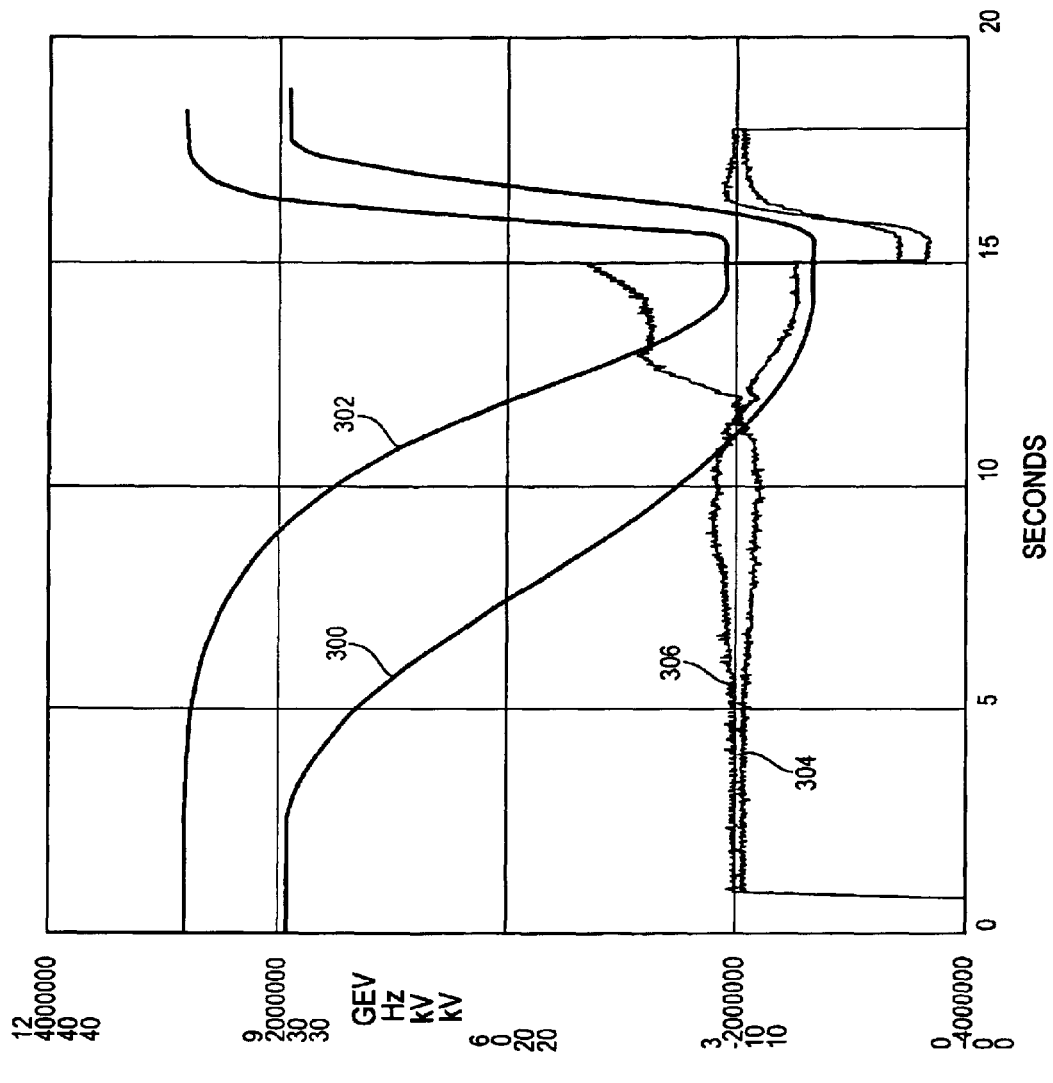
FIG. 3 is beam momentum (I:MMPRQ), radio frequency acceleration system frequency (I:VDSPF0), and radio frequency acceleration system electromagnetic field amplitude (I:H28SUM and I:H28F0) vs. time.

The step of modifying a radio frequency acceleration system 118 can include adding, removing, or altering a radio frequency acceleration system component 142 to ensure that an electromagnetic field 144 of the radio frequency acceleration system follows commands from a computer control system 126. It can also include the adding, removing, or altering a computer control system component 126. It can also include the altering of a value of a variable in a computer control system database 128. In one embodiment of this invention, a modified radio frequency acceleration system 118 is instructed by a modified computer control system 120 to proportionally follow the frequency 204 at which a proton beam circulates around the synchrotron. This frequency decreases as the hadron beam momentum decreases, and reaches a minimum value 206 when the hadron beam momentum has reached its minimum value 202. FIG. 3 shows the result of protons decelerated in the Fermi National Accelerator Laboratory Main Injector synchrotron. The momentum of the proton beam 300 is decelerated over a time duration of 15 seconds. During this time the modified radio frequency acceleration system 118 is generating electromagnetic fields 144 used to decelerate the proton beam and changing its frequency to track the change in proton beam revolution frequency around the Main Injector synchrotron. Extensive modifications to the radio frequency acceleration system 118 and the computer control system 120 were performed in order to keep the magnitude of said electromagnetic fields constant during the 15 seconds. Two measures 304 and 306 of this magnitude are monitored in FIG. 3.

Figure 7:
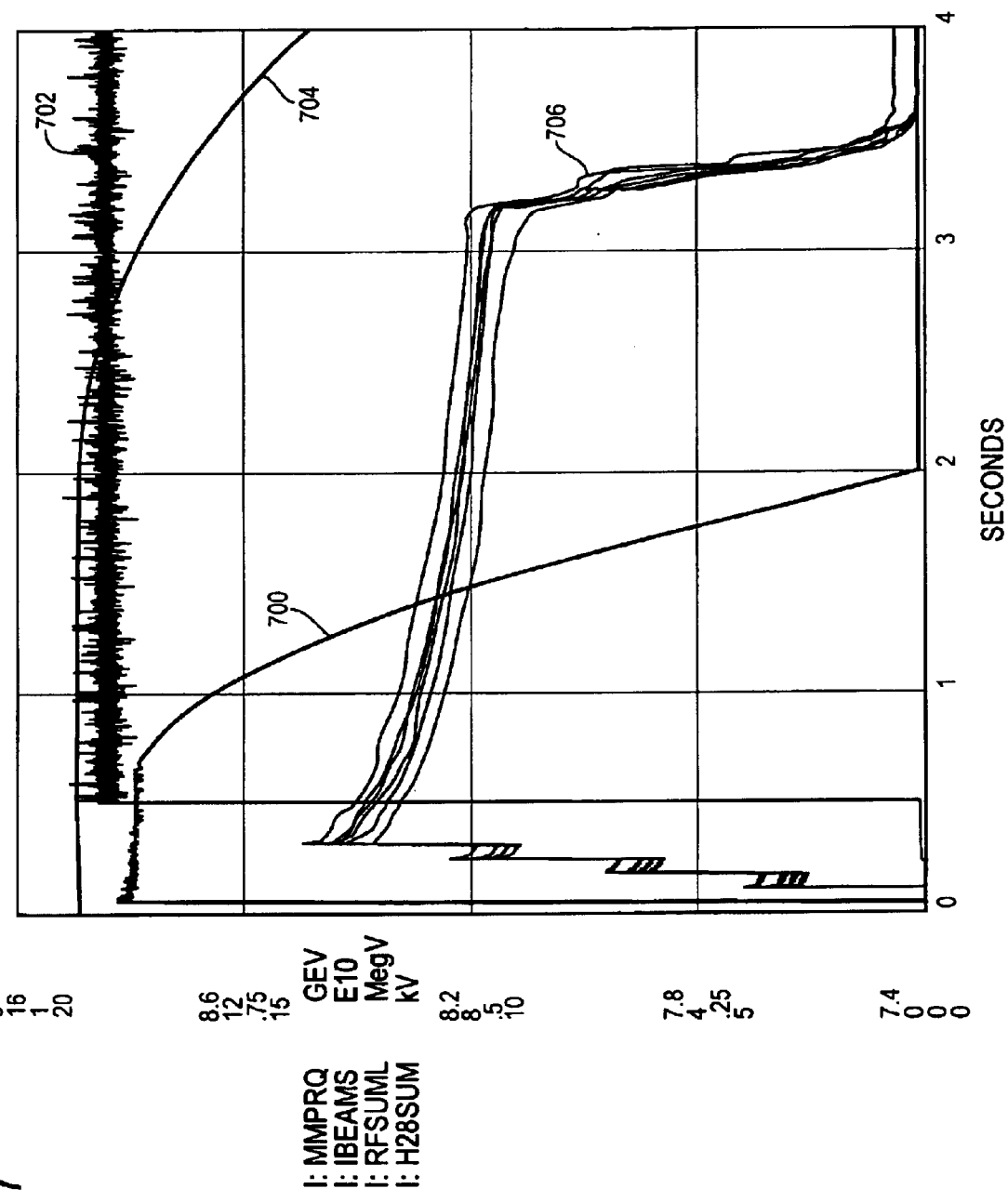
FIG. 7 is radio frequency acceleration system electromagnetic field amplitude (I:RFSUML) used to capture the beam when injected into the synchrotron, radio frequency acceleration system electromagnetic field amplitude (I:H28SUM) used to decelerate the beam, beam momentum (I:MMPRQ), and number of beam particles (beam intensity) in the synchrotron (I:IBEAMS) vs. time.

In another embodiment of this invention, the hadron beam is injected into the synchrotron and controlled by one radio frequency acceleration system and manipulated before the decelerating of the hadron beam begins. FIG. 7 shows such an operation, in which one radio frequency acceleration system has a high initial amplitude 700 that is then gently turned off while the decelerating radio frequency acceleration system is left at a constant amplitude 702 even while the beam momentum 704 is starting to decrease. If modifications to the radio frequency acceleration systems and computer control system 120 are not implemented correctly, the of hadrons circulating in the synchrotron (called intensity 706) will suddenly decrease during the decelerating of the hadron beam.

Figure 8:
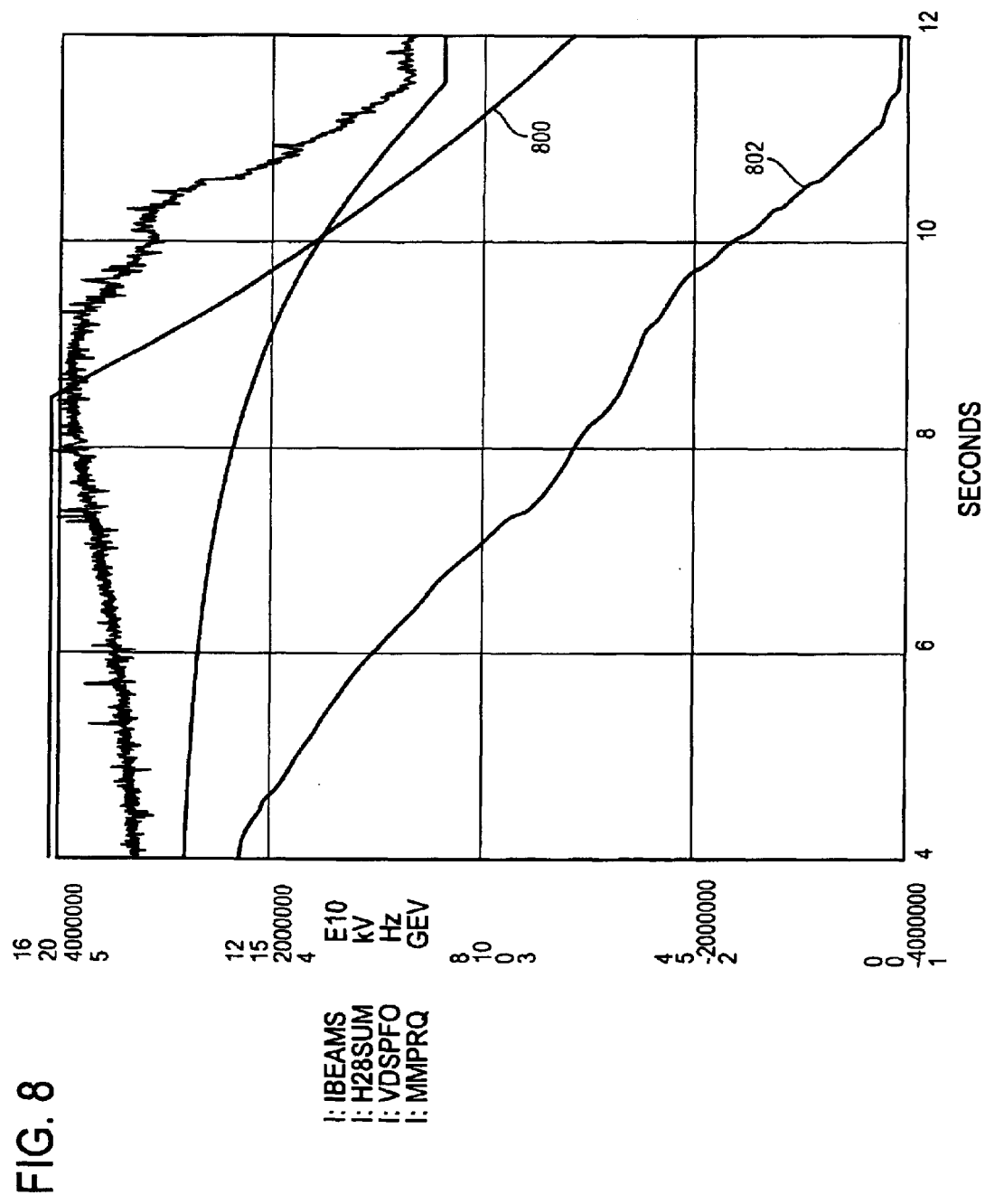
FIG. 8 is beam momentum (I:MMPRQ) and beam intensity (I:IBEAMS) vs. time.

FIG. 8 shows the result of protons decelerated in the Fermi National Accelerator Laboratory Main Injector synchrotron from an initial momentum of 8.889 GeV/c down to 3 GeV/c. At a momentum 800 of 3 GeV/c, labeled I:MMPRQ, the proton beam intensity 802 labeled I:IBEAMS has not yet fallen to zero. Therefore, a small percentage of protons survived a reduction in momentum of almost a factor of three. The cause of this loss of protons during the decelerating of the beam is understood and will be corrected in future decelerations.

When a synchrotron is designed, the first specifications are the minimum and maximum beam momentum. Dipole magnets have a maximum magnetic field. Because the radius of curvature of a hadron beam is proportional to momentum, the radius of the synchrotron is dictated by the maximum magnetic field and the maximum design momentum. On the other hand, dipole magnets have a minimum magnetic field that is determined by the quality of the steel used in its construction. As children find when rubbing steel against a magnet, steel picks up a remnant magnetic field that so distorts the quality of the bending field with uncontrolled quadrupole, sextupole, and higher order field components that cause the beam to fall out of the synchrotron. As a rule of thumb, the limit in the range of momentum in a synchrotron is a factor of 20.

For example, at the Fermi National Accelerator Laboratory (Fermilab) there are three synchrotrons designed to accelerate hadron beams. The Booster has a design minimum (injection) momentum of 0.64 GeV/c and a maximum momentum of 8.9 GeV/c, for an overall momentum range of 14. The Main Injector has a design injection momentum of 8.9 GeV/c and a maximum momentum of 150 GeV/c, for an overall momentum range of 17. Finally, the Tevatron has a design injection momentum of 150 GeV/c and a maximum momentum of 1000 GeV/c, for an overall momentum range of 6.7.

Due to the above magnet limitations, any proposal to inject a hadron beam into an existing synchrotron designed to accelerate beams and then decelerate that beam is greeted with skepticism. For example, in the case of the Fermilab Main Injector one embodiment of this invention has resulted in a demonstrated record synchrotron momentum range of 3 GeV/c to 150 GeV/c, or a factor of 50. Another significant problem with retroactively modifying such a synchrotron to decelerate is the dipole power supply. The amount of electrical current generated by the power supply is proportional to the beam momentum. Therefore, the maximum electrical current is set by the maximum design momentum. In order to decelerate, the dipole power supply system should be capable of generating a noise-free and stable electrical current very near the off-state of the supply, a criteria that the electrical engineers specifying the system never incorporated into their design. Modifications such as the addition, removal, or alteration of filters, regulators, feedback parameters, and control system interface modules should be identified, implemented, and tested. Despite repeated initial misgivings by the designing electrical engineers, FIG. 16 shows the first successful implementation of such modifications, wherein a Fermilab dipole power supply system designed for a maximum electrical current of approximately 9000 Amperes is altered to generate a noise-free and stable current of roughly 100 Amperes.

Quadrupole and sextupole magnets suffer from the same range restrictions in their magnetic field strengths. In addition, their power supplies also generate electrical currents that are roughly proportional to the beam momentum, and hence have the same potential regulation problems as their electrical current are reduced down below their design minimum values. Each power supply needs to be individually assessed and modified in order to generate noise-free and stable electrical current to keep the hadron beam revolving around the synchrotron during the deceleration process.

As shown in FIG. 9, the computer control system that directly commands all elements of the synchrotron should also be modified in order to allow the unanticipated mission of decelerating hadron beams. In this example, the horizontal and vertical tunes are entered by the synchrotron operator from a computer program whose image is in the figure. Normally, the momentum values in the fourth column are ascending in value and with time. In this case, the computer control system database was edited to reflect the reduction in momentum. The computer program was changed to allow for decreasing momentum values and any values below 8.889 GeV/c. The novel aspect of these changes is that unused capabilities of the computer control system hardware were identified wherein the modification did not affect the dozens of other computer programs and control system subsystems that utilized the same hardware. In this way much less effort and disruption to synchrotron operations is used to implement hadron beam deceleration.

Figure 5:
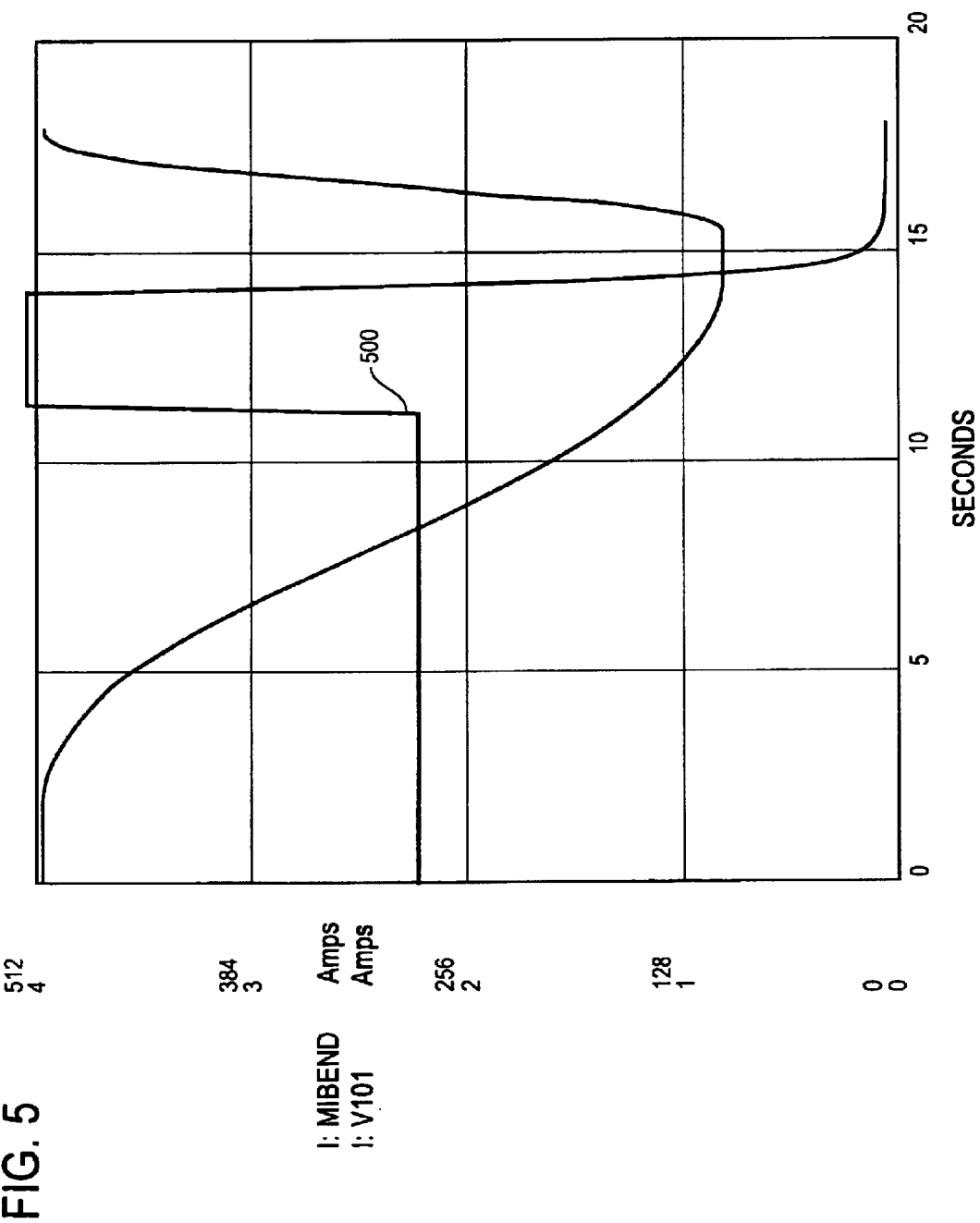
FIG. 5 is dipole corrector power supply system output electrical current (I:V101) vs. time.

The dipole corrector power supplies are similarly controlled by a computer control system. As shown in FIG. 4, the hardware implementing the trajectory control as a function of time and beam momentum had its table entries changed in order to include a separate term using the h01 table that supported deceleration corrections. The I:V101 curve in FIG. 5 shows the implementation of a dipole corrector electrical current change (the curve initially unchanged with the passage of time) during deceleration.

Another challenging synchrotron modification for implementing the unforeseen deceleration of hadron beams is in a radio frequency acceleration system. According to relativity, the higher the momentum of any object, the closer its velocity approaches the speed of light. Because the beam needs to be accelerated every time it passes through the radio frequency acceleration system, the beam needs to see the same portion of the electromagnetic field generated by that system each turn. This characteristic frequency of the electromagnetic field is—an integer multiple of the revolution frequency of the beam around the synchrotron. For example, in the above case of the Fermilab Main Injector the characteristic electromagnetic field frequency difference between the injection and maximum momenta is 0.3 MHz, compared to the characteristic field frequency of 53 MHz. This relatively small change in frequency is anticipated in the design of the cavities within which these electromagnetic fields are generated, and is accommodated by changes in cavity geometry or the addition of passive coils and antenna to modify the cavity characteristics to track this frequency change. These accommodating changes are analogous to changing the length of a trombone in order to support differing resonant tones in the musical instrument.

The shape of the dependence of hadron beam velocity on momentum is highly nonlinear, with very small velocity changes occurring at high momentum and relatively large velocity changes for momenta corresponding to velocitys less than 90% of the speed of light. For example, FIG. 2 shows that during the deceleration of a proton beam in the Fermilab Main Injector from the injection momentum (I:MMPRQ) of 8.9 GeV/c down to 2.0 GeV/c, the radio frequency acceleration system frequency (I:VDSPFO) was changed by 4.7 MHz, a factor of 15 times bigger change than the system design, and in the opposite direction!

In one embodiment of this invention, the computer control system and the radio frequency acceleration system are modified to enable the generation of electromagnetic frequencies below the injection frequency. The issue is then reduced to modifying the response of the associated cavities to produce a sufficient electromagnetic field strength inside the cavity. In the specific embodiment shown in FIG. 3, the lower fuzzy signals are the electromagnetic field strength inside the cavity during the decelerating of the hadron beam when no modifications are made to the cavities whatsoever, but the power levels from the radio frequency amplifiers generating this field was dramatically increased as the electromagnetic field frequency was changed by more than the cavity was designed to accommodate. The two different means of measuring the field strength (I:H28 SUM and I:H28 F0) both indicate it is possible to operate radio frequency acceleration systems in such a mode. The alterations to the radio frequency acceleration system and this result are believed to be so unobvious and contrary to usual approaches of practitioners in the field, and warranted publication of the deceleration results shown in FIG. 8 in the scientific literature.

What is claimed is:

1. A method for using a synchrotron, the method comprising the steps of:

providing a synchrotron designed to accelerate a hadron beam to higher momenta;

altering said synchrotron to enable deceleration of hadron beams to lower momenta; and using the synchrotron in said altering step in decelerating the hadron beam to lower momenta.

2. The method of claim 1, wherein the step of altering includes modifying a dipole power supply system of the synchrotron to maintain a bending magnetic field during the decelerating of the hadron beam.

3. The method of claim 1, wherein the step of altering includes modifying a quadruple power supply system of the synchrotron to maintain focusing and defocusing magnetic fields during the decelerating of the hadron beam.

4. The method of claim 1, wherein the step of altering includes modifying a sextuple power supply system of the synchrotron to maintain chromaticity control during the decelerating of the hadron beam.

5. The method of claim 1, wherein the step of altering includes modifying a dipole corrector power supply system of the synchrotron to maintain a trajectory correction magnetic field during the decelerating of the hadron beam.

6. The method of claim 1, wherein the step of altering includes modifying a radio frequency acceleration system of the synchrotron to impose phase stable momentum reduction during the decelerating of the hadron beam.

7. The method of claim 1, wherein the step of altering includes modifying a computer control system of the synchrotron to enable the decelerating of the hadron beam.

8. The method of claim 1, wherein the step of decelerating is carried out with said hadron beam including protons.

9. The method of claim 1, wherein the step of decelerating is carried out with said hadron beam including antiprotons.

10. The method of claim 1, wherein the step of decelerating is carried out with said hadron beam including atomic ions.

11. The method of claim 2, wherein the step of modifying includes adding a dipole power supply component to ensure that electrical current from the dipole power supply system follows commands from a computer control system.

12. The method of claim 2, wherein the step of modifying includes removing a dipole power supply component to ensure that electrical current from the dipole power supply system follows commands from a computer control system.

13. The method of claim 2, wherein the step of modifying includes altering a dipole power supply component to ensure that electrical current from the dipole power supply system follows commands from a computer control system.

14. The method of claim 2, wherein the step of modifying includes adding a computer control system component to direct the dipole power supply system to follow the commands from said computer control system.

15. The method of claim 2, wherein the step of modifying includes removing a computer control system component to direct the dipole power supply system to follow commands from said computer control system.

16. The method of claim 2, wherein the step of modifying includes altering a computer control system component to direct the dipole power supply system to follow commands from said computer control system.

17. The method of claim 2, wherein the step of modifying includes altering a value of a computer control system database variable to direct the dipole power supply system to follow commands from said computer control system.

18. The method of claim 2, wherein the step of modifying includes altering a byte of information stored in a computer control system component to direct the dipole power supply system to follow commands from said computer control system.

19. The method of claim 2, wherein the step of modifying includes altering a value of a computer control system variable to direct the dipole power supply system to follow commands from said computer control system.

20. The method of claim 3, wherein step of modifying includes adding a quadruple power supply component to ensure that electrical current from the quadruple power supply system follows commands from a computer control system.

21. The method of claim 3, wherein the step of modifying includes removing a quadruple power supply component to ensure that electrical current from the quadruple power supply system follows commands from a computer control system.

22. The method of claim 3, wherein the step of modifying includes altering a quadruple power supply component to ensure that electrical current from the power supply follows commands from a computer control system.

23. The method of claim 3, wherein the step of modifying includes adding a computer control system component to direct the quadruple power supply system to follow the commands from said computer control system.

24. The method of claim 3, wherein the step of modifying includes removing a computer control system component to direct the quadruple power supply system to follow commands from said computer control system.

25. The method of claim 3, wherein the step of modifying includes altering a computer control system component to direct the quadruple power supply system to follow commands from said computer control system.

26. The method of claim 3, wherein the step of modifying includes altering a value of a computer control system database variable to direct the quadruple power supply system to follow commands from said computer control system.

27. The method of claim 3, wherein the step of modifying includes altering a byte of information stored in a computer control system component to direct the quadruple power supply system to follow commands from said computer control system.

28. The method of claim 3, wherein the step of modifying includes altering a value of a computer control system variable to direct the quadruple power supply system to follow commands from said computer control system.

29. The method of claim 4, wherein step of modifying includes adding a sextuple power supply component to ensure that electrical current from the sextuple power supply system follows commands from a computer control system.

30. The method of claim 4, wherein the step of modifying includes removing a sextuple power supply component to ensure that electrical current from the sextuple power supply system follows commands from a computer control system.

31. The method of claim 4, wherein the step of modifying includes altering a sextuple power supply component to ensure that electrical current from the sextuple power supply system follows commands from a computer control system.

32. The method of claim 4, wherein the step of modifying includes adding a computer control system component to direct the sextuple power supply system to follow the commands from said computer control system.

33. The method of claim 4, wherein the step of modifying includes removing a computer control system component to direct the sextuple power supply system to follow commands from said computer control system.

34. The method of claim 4, wherein the step of modifying includes altering a computer control system component to direct the sextuple power supply system to follow commands from said computer control system.

35. The method of claim 4, wherein the step of modifying includes altering a value of a computer control system database variable to direct the sextuple power supply system to follow commands from said computer control system.

36. The method of claim 4, wherein the step of modifying includes altering a byte of information stored in a computer control system component to direct the sextuple power supply system to follow commands from said computer control system.

37. The method of claim 4, wherein the step of modifying includes altering a value of a computer control system variable to direct the sextuple power supply system to follow commands from said computer control system.

38. The method of claim 5, wherein step of modifying includes adding a dipole corrector power supply component to ensure that electrical current from the dipole corrector power supply system follows commands from a computer control system.

39. The method of claim 5, wherein the step of modifying includes removing a dipole corrector power supply component to ensure that electrical current from the dipole corrector power supply system follows commands from a computer control system.

40. The method of claim 5, wherein the step of modifying includes altering a dipole corrector power supply component to ensure that electrical current from the dipole corrector power supply system follows commands from a computer control system.

41. The method of claim 5, wherein the step of modifying includes adding a computer control system component to direct the dipole corrector power supply system to follow the commands from said computer control system.

42. The method of claim 5, wherein the step of modifying includes removing a computer control system component to direct the dipole corrector power supply system to follow commands from said computer control system.

43. The method of claim 5, wherein the step of modifying includes altering a computer control system component to direct the dipole corrector power supply system to follow commands from said computer control system.

44. The method of claim 5, wherein the step of modifying includes altering a value of a computer control system database variable to direct the dipole corrector power supply system to follow commands from said computer control system.

45. The method of claim 5, wherein the step of modifying includes altering a byte of information stored in a computer control system component to direct the dipole corrector power supply system to follow commands from said computer control system.

46. The method of claim 5, wherein the step of modifying includes altering a value of a computer control system variable to direct the dipole corrector power supply system to follow commands from said computer control system.

47. The method of claim 6, wherein step of modifying includes adding a radio frequency acceleration system component to ensure that an electromagnetic field of said radio frequency acceleration system follows commands from a computer control system.

48. The method of claim 6, wherein the step of modifying includes removing a radio frequency acceleration system component to ensure that an electromagnetic field of said radio frequency acceleration system follows commands from a computer control system.

49. The method of claim 6, wherein the step of modifying includes altering a radio frequency acceleration system component to ensure that an electromagnetic field of said radio frequency acceleration system follows commands from a computer control system.

50. The method of claim 6, wherein the step of modifying includes adding a computer control system component to direct the radio frequency acceleration system to follow the commands from said computer control system.

51. The method of claim 6, wherein the step of modifying includes removing a computer control system component to direct the radio frequency acceleration system to follow commands from said computer control system.

52. The method of claim 6, wherein the step of modifying includes altering a computer control system component to direct the radio frequency acceleration system to follow commands from said computer control system.

53. The method of claim 6, wherein the step of modifying includes altering a value of a computer control system database variable to direct the radio frequency acceleration system to follow commands from said computer control system.

54. The method of claim 6, wherein the step of modifying includes altering a byte of information stored in a computer control system component to direct the radio frequency acceleration system to follow commands from said computer control system.

55. The method of claim 6, wherein the step of modifying includes altering a value of a computer control system variable to direct the radio frequency acceleration system to follow commands from said computer control system.

* * * * *